United States Patent
Miller

(10) Patent No.: US 8,913,123 B2
(45) Date of Patent: Dec. 16, 2014

(54) NEEDLE SHIELD POSITIONING SYSTEM AND METHOD

(75) Inventor: Justin Miller, Fountain Hills, AZ (US)

(73) Assignee: West Pharmaceutical Services, Inc., Exton, PA (US)

(*) Notice: Subject to any disclaimer, the term of this patent is extended or adjusted under 35 U.S.C. 154(b) by 383 days.

(21) Appl. No.: 13/423,885

(22) Filed: Mar. 19, 2012

(65) Prior Publication Data

US 2013/0242082 A1 Sep. 19, 2013

(51) Int. Cl.
*H04N 7/18* (2006.01)
*G06T 7/00* (2006.01)
*A61K 51/00* (2006.01)
*A61B 6/03* (2006.01)

(52) U.S. Cl.
CPC ............... *H04N 7/18* (2013.01); *G06T 7/0004* (2013.01); *A61K 51/00* (2013.01); *G06T 2207/20108* (2013.01); *G05B 2219/32368* (2013.01); *A61B 6/03* (2013.01)
USPC ................... 348/94; 348/95; 348/96; 348/97; 348/98; 348/99; 348/47; 348/48; 348/49; 348/50; 348/51; 348/63

(58) Field of Classification Search
CPC ............. H04N 7/18; B23Q 17/22; A61F 2/00
USPC .......................................................... 348/94
See application file for complete search history.

(56) References Cited

U.S. PATENT DOCUMENTS

| | | | | |
|---|---|---|---|---|
| 4,773,412 A * | 9/1988 | Blom | ....................... | 128/207.14 |
| 5,085,647 A * | 2/1992 | Henderson et al. | ........... | 604/192 |
| 5,615,007 A * | 3/1997 | Matsuura et al. | .......... | 356/237.1 |
| 6,629,963 B2 * | 10/2003 | Prais et al. | ..................... | 604/274 |
| 6,651,405 B1 * | 11/2003 | Vetter et al. | ..................... | 53/285 |
| 7,559,919 B2 * | 7/2009 | Pech et al. | ..................... | 604/192 |
| 8,218,724 B2 | 7/2012 | Glocker et al. | | |
| 2006/0189933 A1* | 8/2006 | Alheidt et al. | ................ | 604/110 |
| 2007/0250016 A1* | 10/2007 | Pech et al. | ..................... | 604/198 |
| 2007/0299043 A1* | 12/2007 | Hunter et al. | .................. | 514/171 |
| 2009/0069755 A1* | 3/2009 | Horvath | .......................... | 604/240 |
| 2009/0154789 A1* | 6/2009 | Wolfe | ........................... | 382/141 |

(Continued)

FOREIGN PATENT DOCUMENTS

WO 2009030379 A1 3/2009

*Primary Examiner* — Andy Rao
*Assistant Examiner* — Shan Elahi
(74) *Attorney, Agent, or Firm* — Panitch Schwarze Belisario & Nadel LLP

(57) ABSTRACT

A system for mounting a needle shield to a syringe. The system includes a syringe nest and a gripper having a gripping position and a release position. The gripper is movable between an aligned position and a spaced position. A shaker has a shaker axis that is generally coaxial with the syringe axis. The shaker is movable along the shaker axis. An inspection camera is positioned proximate the syringe axis and defines a line of sight. The syringe nest, gripper, shaker and cap plunger are generally aligned along the syringe axis in a placing configuration wherein the gripper is in the gripping position holding the needle shield. The gripper is in the spaced position and the distal end of the cap plunger is in engagement with the needle shield in a final cap mounting configuration.

20 Claims, 5 Drawing Sheets

(56) References Cited

U.S. PATENT DOCUMENTS

| | | |
|---|---|---|
| 2009/0161941 A1* | 6/2009 | Nakanishi et al. ............ 382/141 |
| 2010/0009022 A1* | 1/2010 | Heinz ............................. 425/94 |
| 2011/0064194 A1 | 3/2011 | Glocker et al. |
| 2011/0178359 A1* | 7/2011 | Hirschman et al. ............... 600/4 |
| 2011/0208126 A1* | 8/2011 | Riemelmoser ................ 604/198 |
| 2012/0045311 A1* | 2/2012 | Lepot ............................ 414/802 |
| 2012/0105620 A1* | 5/2012 | Nakanishi et al. .............. 348/86 |
| 2012/0105621 A1* | 5/2012 | Nakanishi et al. .............. 348/89 |

\* cited by examiner

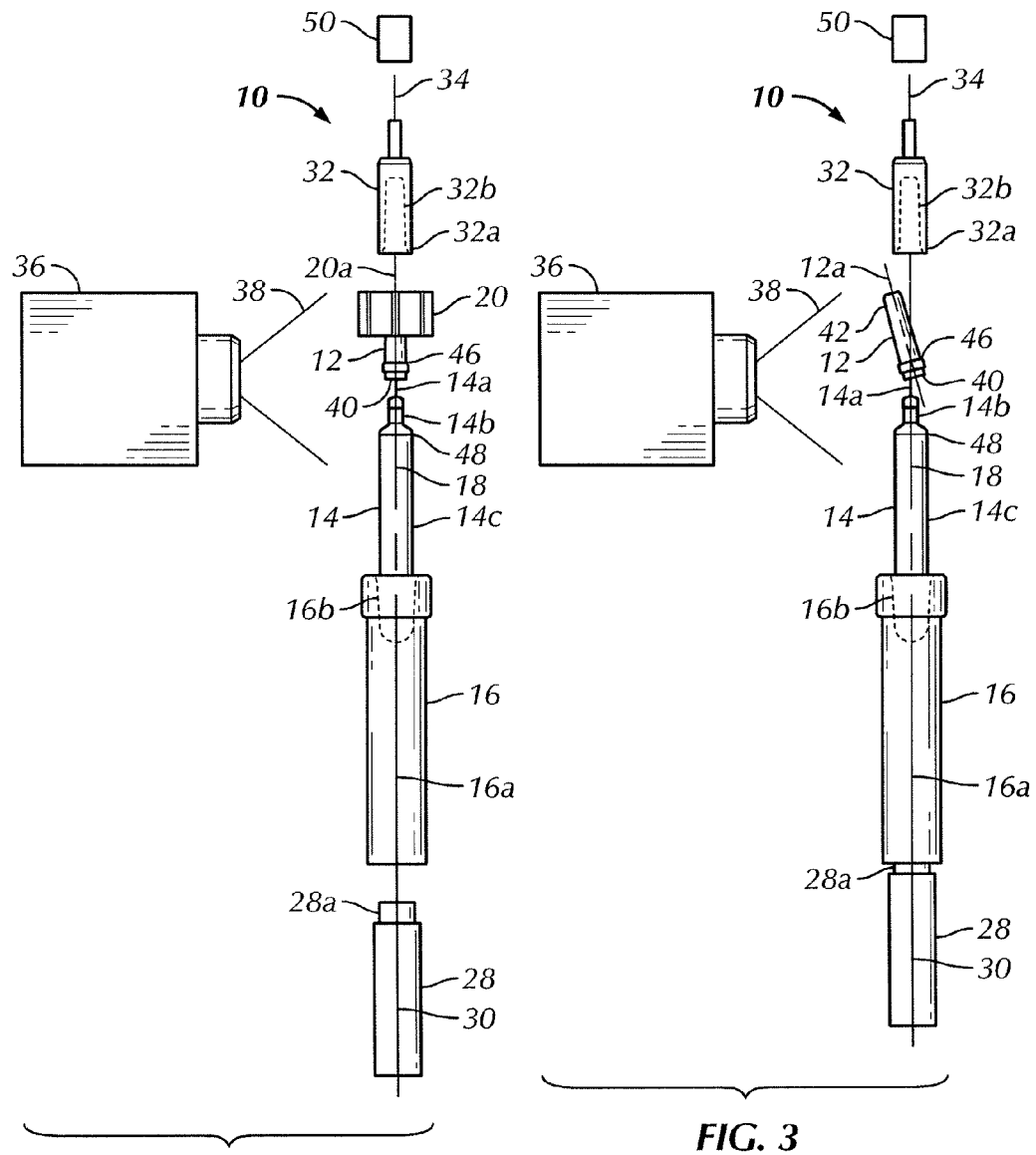

NEEDLE SHIELD POSITIONING SYSTEM AND METHOD

BACKGROUND OF THE INVENTION

Placing needle shields onto syringes is a known process. The needle shields are used to protect a needle of the syringe, limit contamination of the needle and prevent flow of the medication in the syringe out of the needle during shipping. Needle shields have been assembled to syringes by hand and in assembly line-type processes. The hand application processes tend to be inconsistent, labor intensive and may result in exposure of the needle if a worker misorients the needle shield relative to the syringe or applies too much pressure in assembling the needle shield to the syringe, thereby exposing patients to contamination risks.

Certain pick and place methods have also been utilized to mount needle shields onto syringes. Many of these methods have resulted in significant rejections of assembled needle shields and syringes because of misorientation of the needle shields relative to the syringes.

Accordingly, it is desirable to design and implement a system and method for mounting a needle shield onto a syringe that limits rejections of misoriented needle shields relative to the syringes, thereby reliably and properly mounting the needle shields onto the syringes in an assembly line environment.

BRIEF SUMMARY OF THE INVENTION

Briefly stated, the present application is directed to a system for mounting a needle shield to a syringe having a needle with a tip, a collar and a barrel. The system includes a syringe nest for movably supporting the syringe, a gripper having a gripping position and a release position, a shaker having a shaker axis, a cap plunger having a plunger axis and an inspection camera. The syringe nest defines a syringe nest axis. The gripper defines a gripper axis and is movable from an aligned position wherein the gripper axis and syringe axis are generally coaxial to a spaced position. The shaker axis is generally coaxial with the syringe axis and the shaker is movable along the shaker axis. The plunger axis is generally coaxial with the syringe axis. The cap plunger is movable along the plunger axis and includes a distal end. The inspection camera is positioned proximate the syringe axis and defines a line of sight that extends generally through the syringe axis. The syringe nest, gripper, shaker and cap plunger are generally aligned along the syringe axis in a placing configuration wherein the gripper is in the gripping position holding the needle shield. The gripper is in the spaced position and the distal end of the cap plunger is in engagement with the needle shield in a final cap mounting configuration.

In another aspect, the present application is directed to a method of mounting a needle shield to a syringe having a needle with a tip, a collar and a barrel. The needle shield is mounted to the syringe using a system including an inspection mechanism, a cap plunger, a needle shield, a syringe nest, a gripper and a shaker. The syringe has a proximal end and a tip end. The method includes the steps of positioning the proximal end of the syringe in the syringe nest, engaging the needle shield with the gripper in a gripping position, moving the gripper and needle shield from a spaced position to an aligned position wherein the gripper axis of the gripper is aligned generally coaxially with a syringe axis of the syringe, moving the gripper from the gripping position to a released position, thereby causing the needle shield to fall under the force of gravity toward the tip such that the needle shield is positioned on the tip end of the syringe, moving the gripper to a spaced position, moving a distal end of the shaker into engagement with the syringe nest and causing the shaker to vibrate the syringe nest to orient a syringe axis generally coaxially with a shield axis of the needle shield, inspecting the position of the needle shield relative to the syringe with the inspection mechanism and moving the cap plunger into engagement with the needle shield to urge the tip into the needle shield.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is a front elevational, partially exploded view of the system of FIG. 1, showing a gripper positioning the needle shield over a syringe;

FIG. 3 is a front elevational, partially exploded view of the preferred system of FIG. 1, showing a needle shield improperly positioned on the syringe;

DETAILED DESCRIPTION OF THE INVENTION

Figure 1:
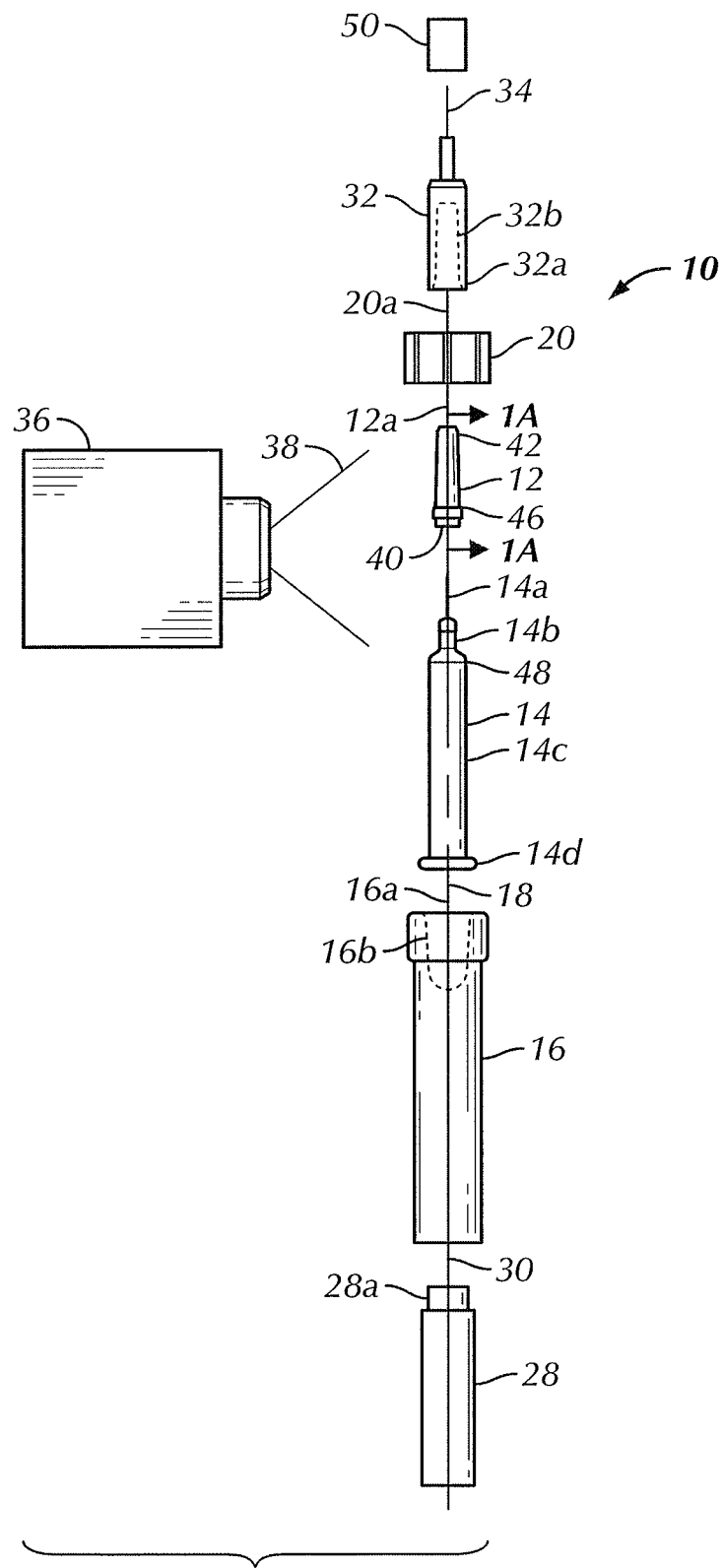
FIG. 1 is a front elevational, partially exploded view of a needle shield positioning system in accordance with a preferred embodiment of the present invention.

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the geometric center or orientation of the system, its components and related parts thereof. The terminology includes the above-listed words, derivatives thereof and words of similar import.

Referring to FIGS. 1-6, the present application is directed to a needle shield positioning system 10 for mounting a needle shield 12 to a syringe 14. The syringe 14 includes a tip 14a, a collar 14b and a barrel 14c having a plunger end 14d. The barrel 14c slidably receives a plunger (not shown) for drawing medication into the syringe 14 and injecting medication into a patient. The syringe 14 is preferably a pre-filled syringe 14 containing a medication placed into the barrel 14c subsequent to mounting the needle shield 12 thereon, but prior to distribution of the pre-filled syringe 14 to the end user. The needle shield 12 operates in part to seal the tip 14a of the pre-filled syringe 14. However, the syringe 14 is not limited to being a pre-filled syringe or even a syringe filled at the point of use, but could be any drug injection device comprising a needle or cannula where providing a needle shield 12 is desirable.

Figure 1A:
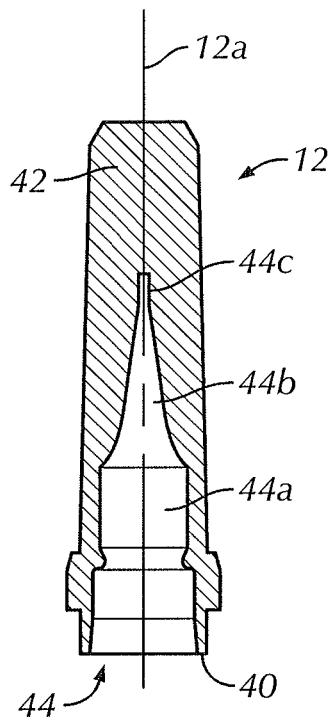
FIG. 1A is an enlarged cross-sectional view of a first preferred needle shield of the preferred needle shield positioning system of FIG. 1, taken along line 1A-1A of FIG. 1.

Referring to FIGS. 1 and 1A, in the preferred embodiment, the needle shield 12 is constructed of a relatively elastic and pliable material, such as a rubber-like material. The needle shield 12 is preferably constructed of this relatively elastic or soft rubber-like material in an injection molding process and is formed into the general size and shape of the preferred needle shield 12 using this injection molding process. However, the needle shield 12 is not so limited and may be otherwise configured as long as the needle shield 12 is able to be mounted to the syringe 14 to cover the tip 14a in a final cap mounting configuration.

Figure 1B:
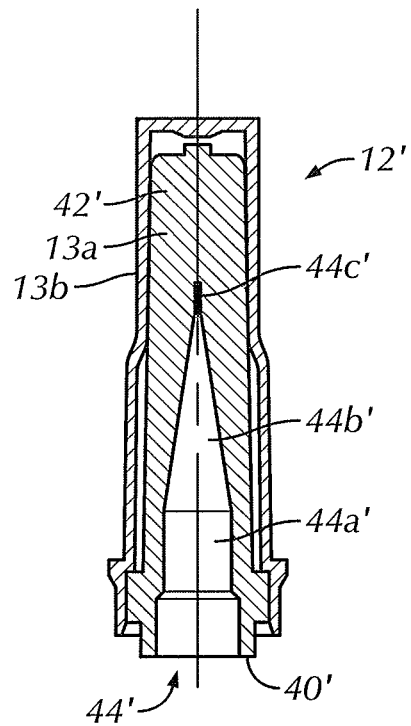
FIG. 1B is an enlarged cross-sectional view of a second preferred needle shield of the preferred needle shield positioning system of FIG. 1, taken along line 1A-1A of FIG. 1.

Referring to FIG. 1B, in a second preferred embodiment of the needle shield 12', which is distinguished from the first preferred embodiment of the needle shield 12 by utilizing a prime symbol (') with like reference numerals identifying like elements, the second preferred needle shield 12' includes a relatively soft plug 13a mounted within a generally rigid polymeric shell 13b. The plug 13a may be fixed within the shell 13b or may be loosely secured within the shell 13b. The system 10 of the preferred embodiment is adjustable for use with either the first and/or second preferred needle shields 12, 12'. The system 10 is described herein with reference to the first preferred needle shield 12, it being understood that the system 10 preferably operates equally as well with the needle shield 12' of the second preferred embodiment.

Referring to FIGS. 1-6, the preferred needle shield positioning system 10 includes a syringe nest 16 for movably supporting the syringe 14. The syringe nest 16 defines a syringe axis 16a that extends generally longitudinally along an through the syringe nest 16. The syringe nest 16 also preferably includes a nest cavity 16b therein that receives at least a portion of the plunger end 14d of the syringe 14 to secure the syringe 14 to the syringe nest 16 in an operating configuration. The syringe 14 is preferably secured relative to the syringe nest 16 in the operational configuration such that a syringe axis 18 is generally coaxial with a syringe nest axis 16a. The syringe 14 is preferably secured to the syringe nest 16 in the operational configuration such that the syringe 14 is movable along the syringe nest axis 16a away from the syringe nest 16 to remove the syringe 14 from the syringe nest 16.

The preferred needle shield positioning system 10 preferably includes a plurality (not shown) of the syringe nests 16 and syringes 14 moving in an assembly line-like operation for mounting multiple needle shields 12 to multiple syringes 14 for shipping or generally to protect the tips 14a of the syringes 14, in a manner generally understood by those having ordinary skill in the art.

The preferred system 10 also includes a gripper 20 having a gripping position for grasping the needle shield 12 and a release position, wherein the gripper 20 is configured such that it does not grasp and hold the needle shield 12 or releases the needle shield 12. The gripper 20 defines a gripper axis 20a. The gripper 20 is movable from an aligned position (FIGS. 1 and 2) wherein the gripper axis 20a and the syringe axis 18 are generally coaxial to a spaced position (FIGS. 3-6) wherein the gripper 20 is spaced from the syringe axis 18 and the gripper axis 20a is not coaxial or generally coaxial with the syringe axis 18. The gripper 20 of the preferred embodiment is able to move in numerous degrees of freedom in order to grasp the needle shield 12, align the needle shield 12 over the syringe 14 for placement of the needle shield 12 on the tip 14a and away from the needle shield 12 to pick up an additional needle shield 12 for placement on another syringe 14. Accordingly, the gripper 20 generally acts as a pick and place robot for positioning and placing the needle shield 12 on the syringe 14.

Figure 2A:
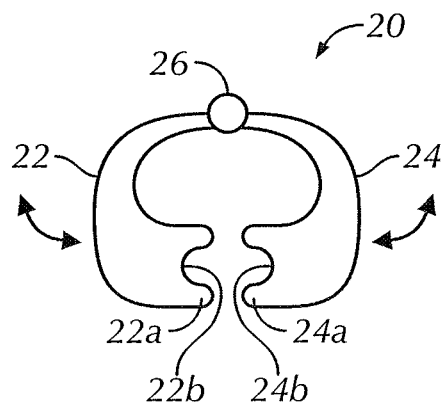
FIG. 2A is a top plan view of a gripper of the system of FIG. 1.

Referring to FIGS. 1-2A, the gripper 20 of the preferred embodiment includes first and second arms 22, 24 that are pivotable relative to each other. The first and second arms 22, 24 have first and second terminal ends 22a, 24a. When the first and second arms 22, 24 pivot relative to each other at a pivot joint 26, the first and second terminal ends 22a, 24a move relative to each other. The first and second terminal ends 22a, 24a are closer to each other in the gripping position than in the released position. The first and second terminal ends 22a, 24a include concave surfaces 22b, 24b, respectively, that are designed and configured to engage and grip the needle shield 12. The gripper 20 is not limited to the inclusion of the preferred first and second arms 22, 24 with the first and second terminal ends 22a, 24a and the concave surfaces 22b, 24b for engaging the needle shield 12. The gripper 20 may be comprised of nearly any component that is able to engage and disengage with the needle shield 12 for picking and placing the needle shield 12, such as a suction device, radially expanding device or other like devices.

In the preferred embodiment, the gripper 20 is pneumatically driven or driven by air power. Specifically, the preferred first and second arms 22, 24 are driven to and between the gripping and released positions by pneumatic pressure. The gripper 20 is not limited to being pneumatically driven and may be mechanically, hydraulically or otherwise driven to and between the gripping and release positions and in its other movements to pick and place the needle shield 12.

Referring to FIGS. 1-2, the needle shield positioning system 10, at its lower end, also includes a shaker 28 having a shaker axis 30 that is generally coaxial with the syringe axis 18 in a working configuration. The shaker 28 is preferably linearly movable along the shaker axis 30. The shaker 28 is not limited to having its shaker axis 30 coaxial with the syringe axis 18 in the working configuration and the syringe axis 30 may be spaced or otherwise positioned relative to the shaker axis 30 depending upon the operation of the device. However, during operation of the shaker 28 for shaking the syringe nest 16, the shaker axis 30 is preferably at least parallel to the syringe axis 18 and, more preferably, coaxial with the syringe axis 18, which will be described in greater detail below.

In the preferred embodiment, the shaker 28 is preferably comprised of a pneumatic vibrator 28. The shaker or pneumatic vibrator 28 is preferably movable into facing engagement with the syringe nest 16 such that the syringe nest 16 may be vibrated by the shaker 28. The shaker 28 is not limited to being comprised of the pneumatic vibrator 28 and may be comprised of nearly any component that is able to apply a vibrational-type motion to the syringe nest 16, syringe 14 and/or needle shield 12 during use. For example, the shaker 28 may be comprised of an acoustic horn that applies vibration to the syringe nest 16, syringe 14 and needle shield 12 during use. The shaker 28 may be comprised of nearly any component that is able to vibrate the syringe nest 16, syringe 14 and/or needle shield 12 to orient the needle shield 12 relative to the syringe 14 as will be described in greater detail below.

The needle shield positioning system 10 also includes a cap plunger 32 having a plunger axis 34 that is generally coaxial with the syringe axis 18 in the working configuration. The cap plunger 32 is movable along the plunger axis 34 and is preferably positioned above the needle shield 12, syringe 14, syringe nest 16 and shaker 28 in the working configuration. The cap plunger 32 includes a distal end 32a that faces the needle shield 12 in the working configuration. The distal end 32a is designed and configured to engage the needle shield 12 and urge the needle shield 12 toward the syringe 14. The distal end 32a may be designed and configured to have a complementary concave indentation 32b that forms or engages around the end of the needle shield 12 to precisely engage the needle shield 12 and align a needle shield axis 12a with the plunger axis 34, generally coaxially. Shaping the complementary concave indentation 32b of the blunt distal end 32a to precisely engage the external surface of the needle shield 12 preferably ensures proper positioning of the needle shield 12 relative to the cap plunger 32 and movement of the needle shield 12 and cap plunger 32 in unison during use, as will be described in greater detail below.

The needle shield positioning system 10 also includes an inspection camera 36 positioned proximate the syringe axis 18. The inspection camera 36 defines a line of sight 38 that extends generally through the syringe axis 18. The inspection camera 36 is preferably designed and configured to visually capture information related to the positioning of the needle shield 12 relative to the syringe 14. Specifically, the inspection camera 36 is designed and configured to verify proper positioning of the needle shield 12 relative to the syringe 14 during the assembly process or indicate that the needle shield 12 is improperly positioned relative to the syringe 14 such that a correction can be made or the syringe 14 and needle shield 12 combination can be rejected, as will be described in greater detail below.

The syringe nest 16, gripper 20, shaker 28 and cap plunger 32 are generally aligned along the syringe axis 18 in a placing configuration (FIG. 2). In the placing configuration, the gripper 20 is in the gripping position holding the needle shield 12 above the syringe 14. The needle shield 12 is preferably positioned with the needle shield axis 12a coaxial with the syringe axis 18 in the placing configuration and the needle shield 12 is preferably positioned such that an open end 40 is facing the syringe 14. The gripper 20 moves to the release position prior to moving out of the placing configuration to drop the needle shield 12, under the force of gravity, onto the syringe 14 to initially mount the needle shield 12 on the syringe 14, as shown in FIG. 4, as will be described in greater detail below.

In the preferred embodiment, the line of sight 38 is generally perpendicular to the syringe axis 18 and extends through the needle shield 12 and the tip 14a of the syringe 14 in an inspection configuration (FIGS. 3-6). The line of sight 38 is preferably perpendicular to and extends through the needle shield 12 and tip 14a of the syringe 14 such that the positioning along the syringe axis 18 of the needle shield 12 relative to the syringe 14 and the orientation of the needle shield 12 relative to the syringe 14 can be inspected by the inspection camera 36. The line of sight 38 is not limited to being generally perpendicular to the syringe axis 18 and may be oriented at nearly any angle relative to the syringe axis 18 for inspecting the positioning of the needle shield 12 relative to the syringe 14.

Figures 4, 5:
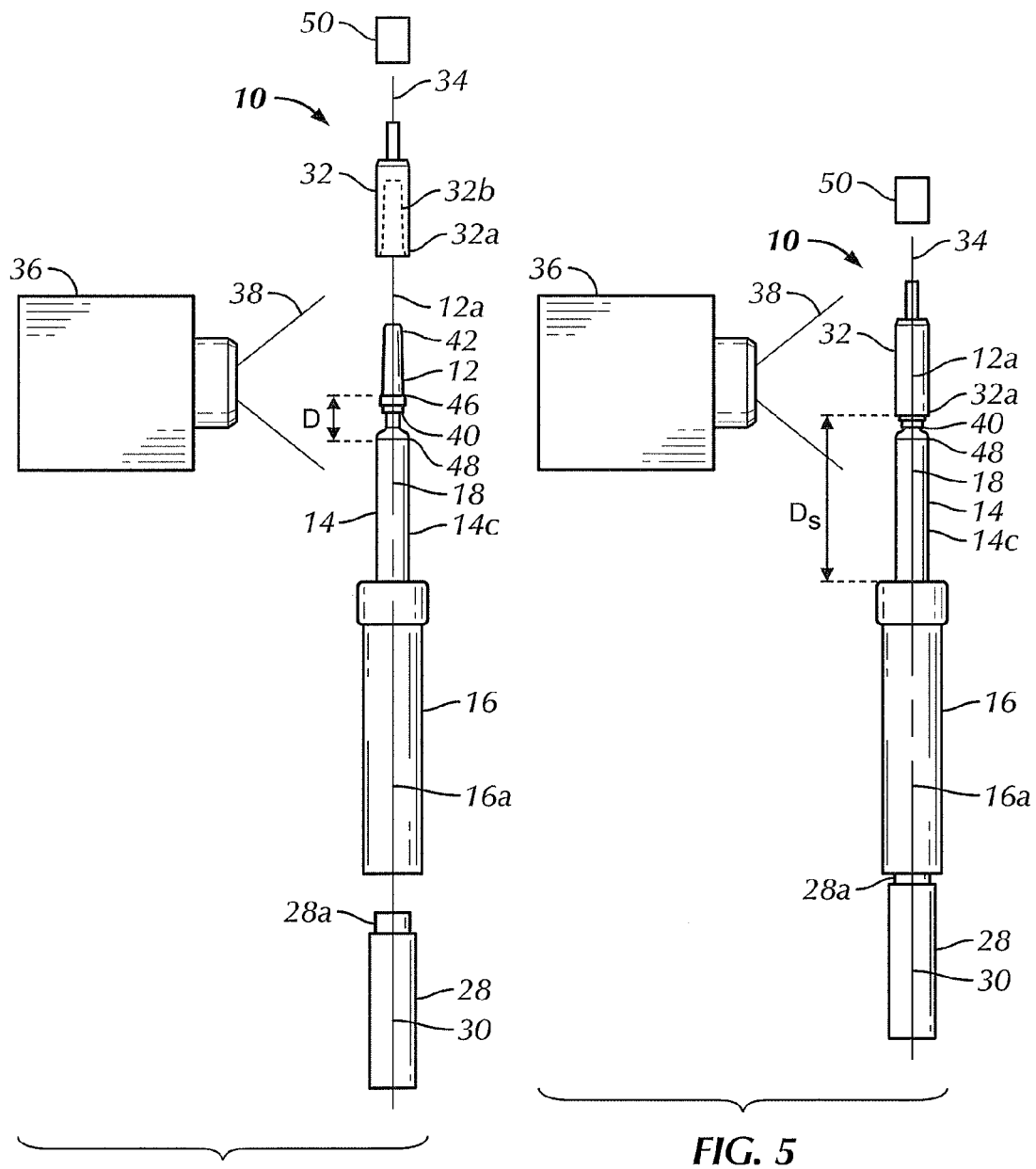
FIG. 4 is a front elevational view, partially exploded of the system of FIG. 1, showing the needle shield initially positioned on the syringe.
FIG. 5 is a front elevational, partially exploded view of the system of FIG. 1, showing a plunger urging the needle shield onto the syringe.
Figure 6:
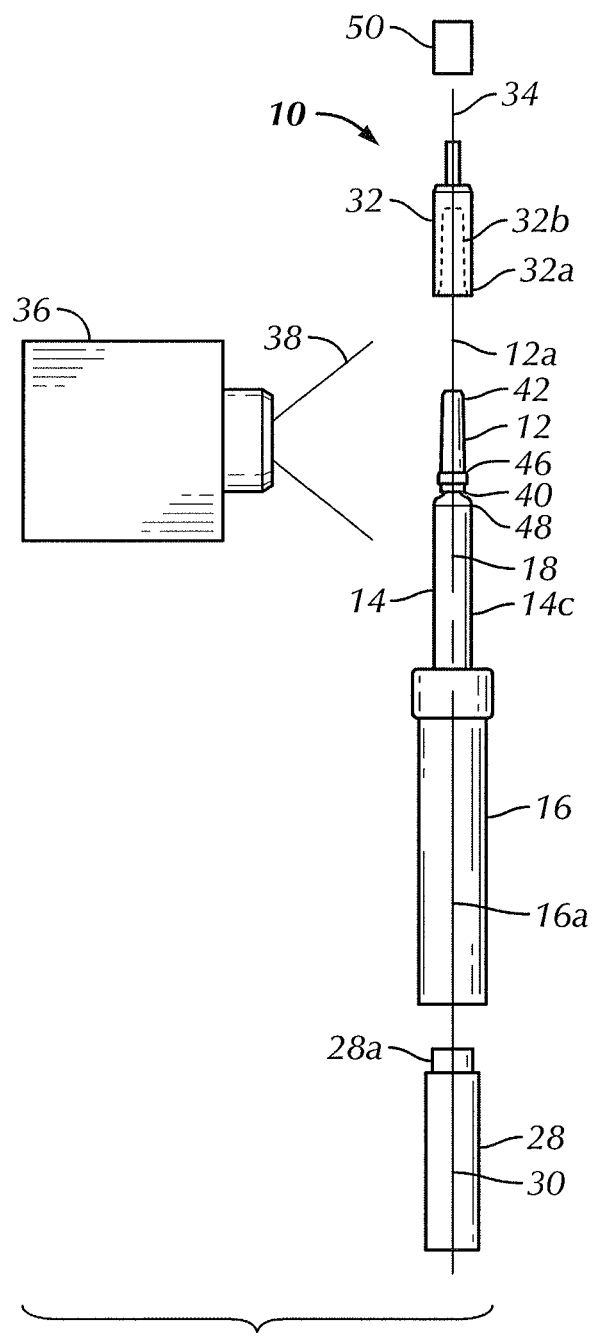
FIG. 6 is a front elevational, partially exploded view of the system of FIG. 1 with the needle shield finally mounted to the syringe.

The gripper 20 is in the spaced position and the distal end 32a of the cap plunger 32 is in engagement with the needle shield 12 in a final cap mounting configuration (FIG. 5). The concave indentation 32b of the shaped distal end 32a preferably complementarily mates with the outer surface of the needle shield 12 to ensure proper positioning of the needle shield 12 relative to the cap plunger 32 in the final cap mounting configuration. The positioning of the cap plunger 32 relative to the needle shield 12 is preferably configured such that the needle shield axis 12a is coaxial with the plunger axis 34, both of which are coaxial with the syringe axis 18 in the final cap mounting configuration. Such a configuration is preferred such that the needle shield 12 is properly positioned for mounting to the syringe 14.

Referring to FIG. 1A, the needle shield 12 of the first preferred embodiment includes a closed end 42 opposite the open end 40 and a central cavity 44 extending longitudinally along the needle shield axis 12a from the open end 40 toward the closed end 42. The central cavity 44 includes a first cylindrical section 44a proximate the open end 40, a narrowing conical section 44b and a second cylindrical section 44c that has a smaller diameter than the first conical section 44a. In the final cap mounting configuration, the first cylindrical section 44a is preferably engaged with the collar 14b and/or barrel 14c of the syringe 14, the shaft of the needle is positioned in the second cylindrical section 44c and the tip 14a is preferably embedded in the closed end 42 beyond the second cylindrical section 44c of the central cavity 44. Accordingly, the tip 14a is blocked by the material of the closed end 42, thereby containing the drug within the syringe 14 and generally preventing the drug from flowing out of the tip 14a. In addition, the tip 14a and the associated needle are generally protected from contamination and/or mechanical damage by the needle shield 12.

Referring to FIG. 1B in the second preferred embodiment, the needle shield 12' is comprised of a rigid needle shield including the plug 13a and the relatively hard shell 13b. The central cavity 44' is preferably similarly configured to engage the syringe 14, plug the tip 14a and generally protect the needle and tip 14a from contamination and mechanical damage. The generally rigid shell 13b provides a more rigid covering and protector for the needle and tip 14a.

Referring to FIGS. 1-6, in operation, the preferred needle shield positioning system 10 is utilized to pick a needle shield 12, orient the needle shield 12 on the syringe 14 and engage the needle shield 12 with the syringe in the final cap mounting configuration. In this operation, the syringe 14 is positioned with its plunger end 14d in the syringe nest 16. In this configuration, the syringe axis 18 is preferably coaxial or at least parallel to the syringe nest axis 16a, with the tip 14a spaced from the syringe nest 16. The plunger end 14d is preferably positioned at least partially in the nest cavity 16b to maintain the generally parallel or coaxial relationship between the syringe axis 18 and the syringe nest axis 16a.

The syringe nest 16 and syringe 14 are preferably moved to a position proximate the inspection camera 36 and gripper 20. The gripper 20 engages the needle shield 20 in the gripping position and moves from the spaced position to an aligned position wherein the gripper axis 20a is generally parallel or coaxial with the syringe axis 18. In this aligned position, the central cavity 44 of the needle shield 12 is facing the tip 14a and the needle shield axis 12a is preferably coaxial with the syringe axis 18. The gripper 20 is moved from the gripping position to the release position, thereby causing the needle shield 12 to fall under the force of gravity toward the tip 14a such that the needle shield 12 is positioned on the tip 14a of the syringe 14. Following this drop of the needle shield 12, the tip 14a is preferably positioned in the second cylindrical section 44a of the central cavity 44. After dropping the needle shield 12, the gripper 20 moves to the spaced position, preferably to pick or grasp another needle shield 12 for placement over another syringe 14.

The shaker 28 is then moved into contact with the syringe nest 16, such that a drive end 28a of the shaker 28 is in contact with the syringe nest 16. The shaker 28 is preferably pneumatically driven to shake or vibrate the syringe nest 16, thereby shaking the associated syringe 14 and needle shield 12. The syringe nest 16, syringe 14 and needle shield 12 are vibrated or shaken to urge the needle shield 12 into proper orientation relative to the syringe 14 such that the needle shield axis 12a is generally coaxial with the syringe axis 18. In addition, the tip 14a is preferably urged, through the shaking, into the second cylindrical section 44c. The diameter of the second cylindrical section 44c is preferably approximately the same or slightly larger than a diameter of the needle of the syringe 14. This vibration or shaking of the syringe 14 and needle shield 12 urges the tip 14a along the conical section 44b and into the second cylindrical section 44c, particularly if the tip 14a is not positioned in the second cylindrical section 44c after initially being dropped onto the syringe 14.

The orientation of the needle shield 12 relative to the syringe 14 may be inspected by the inspection camera 36 prior to shaking and is preferably inspected following shaking. Referring specifically to FIG. 3, the inspection camera 36 may determine that the needle shield 12 is misoriented relative to the syringe 14 and requires additional vibration input from the shaker 28. In addition, the inspection camera 36 may determine, following inspection, that the orientation of the needle shield 12 relative to the syringe 14 may not be corrected and the individual syringe 14 and needle shield 12 assembly may be rejected or sent for rework. In the preferred embodiment, the syringe nest 16, syringe 14 and needle shield 12 may be rotated about the syringe axis 18 and/or the syringe nest axis 16a such that the inspection camera 36 may inspect the positioning of the syringe 14 relative to the needle shield 12 from various angles.

The inspection camera 36 is not limited to specifically being a visual inspection mechanism and may be comprised of nearly any variety of inspection mechanism 36 that is able to determine the orientation and positioning of the syringe 14 relative to the needle shield 12. For example, the inspection camera 36 may be comprised of a mechanical inspection mechanism, such as an optical system, that determines orientation of the needle shield axis 12a relative to the syringe axis 18 or various positions of the needle shield 12 relative to locations on the syringe 14. For example, the position of the open end 40 relative to the barrel 14c of the syringe 14 may be determined by a mechanical inspection mechanism. Further, the inspection camera 36 may be comprised of an x-ray inspection mechanism that determines the position of the needle shield 12 relative to the syringe 14. In addition, the inspection camera 36 may measure a distance D between a first reference mark 46 on the needle shield 12 and a second reference mark 48 on the syringe 14 to ensure proper positioning of the needle shield 12 relative to the syringe 14.

Following this inspection, the syringe 14 and needle shield 12 may be further shaken to properly orient the needle shield 12 relative to the syringe 14 or may be rejected for rework or further processing. When the inspection reveals that the needle shield 12 is properly positioned relative to the syringe 14, the shaker 28 is preferably moved out of engagement with the syringe nest 16 and the cap plunger 32 is moved into engagement with the closed end 42 of the needle shield 12 to urge the needle shield 12 toward the syringe 14 and the tip 14a into the closed end 42. The indentation 32b of the distal end 32a of the cap plunger 32 is complementarily shaped to receive the closed end 42 and coaxially orient the needle shield axis 12a to the plunger axis 34. The cap plunger 32 urges the needle shield 12 toward the syringe 14 such that the tip 14a moves into the closed end 42 with the tip 14a embedded in the material of the needle shield 12.

The inspection camera 36 again, preferably inspects the positioning of the needle shield 12 relative to the syringe 14 to verify that the needle shield 12 is properly positioned relative to the syringe 14. These inspections preferably occur at various angles relative to the mounted syringe 14 and needle shield 12. In this final cap mounting configuration, the needle of the syringe 14 is preferably positioned at least partially within the second cylindrical section 44c with the tip 14a in the closed end 42 and the collar 14b and/or barrel 14c in the first cylindrical section 44a. In the final cap mounting configuration, the tip 14a is blocked from leaking medication from the barrel 14c by the closed end 42 and any leakage into the central cavity 44 is generally held therein because the first cylindrical section 44a seals with the collar 14b and/or barrel 14c. Further, the tip 14a and any component of the syringe 14 positioned within the or in contact with the central cavity 44 is generally protected from contamination for shipping purposes.

The cap plunger 32 is preferably moved out of engagement with the needle shield 12 and the assembled syringe 14 and needle shield 12 are packaged for shipping. The needle shield positioning system 10 subsequently mounts additional needle shields 12 onto additional syringes 14.

Referring specifically to FIG. 3, following dropping of the needle shield 12 onto the syringe 14, the inspection camera 36 is preferably able to determine the orientation of the needle shield axis 12a relative to the syringe axis 18 and whether this orientation falls outside of acceptable tolerances. If the orientation of the needle shield 12 relative to the syringe 14 falls outside of acceptable tolerances, such as the orientation that is shown in FIG. 3, the shaker 28 may be actuated to shake the syringe nest 16, syringe 14 and needle shield 12 to urge the needle shield 12 into proper orientation relative to the syringe 14. These vibrations or shaking urge the needle shield 12 toward the or into proper orientation relative to the syringe 14 by urging the tip 14a along the conical section 44b and toward the second cylindrical section 44c. Simply pushing the needle shield 12 toward the syringe 14 when in the inappropriate orientation shown in FIG. 3, may cause the tip 14a to extend into the needle shield 12 at an improper orientation which may result in a tip 14a being exposed outside of the needle shield 12 in extreme situations. Accordingly, the shaker 28 urges this proper orientation and limits rejections of assembled needle shields 12 and syringes 14 due to improper orientation. If the improper orientation is not remedied by the shaker 28, the needle shield 12 and syringe 14 may be disengaged from each other and subsequently reengaged in a proper orientation, thereby preventing complete loss of the components.

Following proper positioning of the needle shield 12 relative to the syringe 14 in the final cap mounting configuration, the assembled syringe 14 and needle shield 12 are removed from the syringe nest 16 for distribution to patients.

Referring to FIGS. 4 and 5, in the preferred embodiment, the cap plunger 32 is in a withdrawn position when spaced from the needle shield 12 (FIG. 4) and moves to a seating position (FIG. 5) to urge the needle shield 12 into the final cap mounting position. In the seating position, the cap plunger 32 is positioned at a predetermined seating distance $D_S$ from the syringe nest 16. The seating distance $D_S$ may be utilized as part of an inspection process to confirm or at least partially confirm the positioning of the needle shield 12 relative to the syringe 14. The seating distance $D_S$ is preferably determined depending upon the size of the syringe 14 and needle shield 12 and/or the configuration of the cap plunger 32 and syringe nest 16. In the preferred operation, the cap plunger 32 moves from the withdrawn position to the seating position and back to the withdrawn position when moving the needle shield 12 into the final cap mounting position.

After the inspection camera 36 verifies the orientation of the needle shield 12 relative to the syringe 14 in the final cap mounting configuration, the syringe 14 and attached needle shield 12 are preferably further inspected by an x-ray inspection mechanism 50. The x-ray inspection mechanism 50 is preferably oriented along the syringe axis to verify the positioning of the tip 14a relative to the syringe axis 18. Accordingly, the x-ray inspection mechanism 50 verifies the position of the tip 14a relative to the syringe axis 18. In the preferred embodiment, the tip 14a is preferably within or positioned within one millimeter (1 mm) from the syringe axis 18 in the final mounting configuration. If the tip 14a is spaced further than one millimeter (1 mm) from the syringe axis 18 in the final cap mounting configuration, the assembled needle shield 12 and syringe 14 are rejected and either reworked or disposed. The x-ray inspection mechanism 50 and its inspection are not limiting and the x-ray inspection may not be conducted or the tolerance may be otherwise set depending upon various factors of the design.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A system for mounting a needle shield to a syringe defining a syringe axis and having a needle with a tip, a collar and a barrel, the system comprising:
    a syringe nest including a nest cavity for movably supporting a plunger end of the syringe, the syringe nest defining a syringe nest axis that is substantially aligned with the syringe axis;
    a gripper including a first arm pivotable relative to a second arm, the first arm having a first concave surface and the second arm having a second concave surface, the gripper having a gripping position and a release position, the gripper defining a gripper axis, the gripper movable from an aligned position wherein the gripper axis and syringe axis are generally coaxial and a spaced position;
    a shaker having a shaker axis that is generally coaxial with the syringe axis, the shaker having a drive end and being movable along the shaker axis such that the drive end is selectively in contact with the syringe nest;
    a cap plunger having a plunger axis that is generally coaxial with the syringe axis and being substantially aligned with the syringe nest axis, the cap plunger movable along the plunger axis, the cap plunger including a distal end; and
    an inspection camera positioned proximate the syringe axis and defining a line of sight that extends generally through the needle shield, the inspection camera configured for inspecting a position of the needle shield proximate the syringe axis, the syringe nest, gripper, shaker and cap plunger being generally aligned along the syringe axis in a placing configuration wherein the gripper is in the gripping position holding the needle shield between the first and second concave surfaces, the gripper being in the spaced position and the distal end of the cap plunger being in engagement with the needle shield in a final cap mounting configuration.

2. The system of claim 1 wherein the first and second arms have first and second terminal ends, respectively, the first and second terminal ends being closer to each other in the gripping position than in the release position.

3. The system of claim 1 wherein the line of sight is generally perpendicular to the syringe axis and extends through the needle shield and a tip end of the syringe in an inspection configuration.

4. The system of claim 1 wherein the shaker is comprised of a pneumatic vibrator.

5. The system of claim 1 wherein the drive end of the shaker is movable into facing engagement with the syringe nest.

6. The system of claim 1 wherein the needle shield includes a generally rigid polymeric shell and a relatively soft plug mounted within the shell.

7. The system of claim 1 wherein the gripper is in the gripping position in the placing configuration and moves to the release position prior to moving out of the placing configuration.

8. The system of claim 1 wherein the gripper is comprised of a pneumatic gripper.

9. A method of mounting a needle shield to a syringe having a needle with a tip, a collar and a barrel using a system including an inspection camera, a cap plunger, the needle shield, a syringe nest having a nest cavity, a gripper having a first arm pivotable relative to a second arm and a shaker having a drive end, the syringe having a proximal end and a tip end, the method comprising:
    (a) positioning the proximal end of the syringe in the nest cavity of the syringe nest;
    (b) engaging the needle shield with the gripper in a gripping position by pivoting a first terminal end of the first arm toward a second terminal end of the second arm, such that the first terminal end and the second terminal end engage the needle shield;
    (c) moving the gripper and needle shield from a spaced position to an aligned position wherein the a gripper axis of the gripper is aligned generally parallel with a syringe axis of the syringe;
    (d) moving the gripper from the gripping position to a release position by moving the first terminal end away from the second terminal end, causing the needle shield to fall under the force of gravity toward the tip such that the needle shield is positioned on the tip end of the syringe;
    (e) moving the gripper to a spaced position;
    (f) moving the drive end of the shaker into engagement with the syringe nest and causing the shaker to vibrate the syringe nest to orient a syringe axis generally coaxially with a shield axis of the needle shield;
    (g) inspecting the position of the needle shield relative to the syringe with the inspection camera; and
    (h) moving the cap plunger into engagement with the needle shield, which includes a plug mounted inside a shell, to urge the needle shield toward the syringe and the tip into the plug.

10. The method of claim 9 further comprising:
    (i) moving the cap plunger away from the needle shield and repeating step (g).

11. The method of claim 10 wherein the inspection camera optically measures a position of the needle shield relative to the syringe in step (g).

12. The method of claim 9 wherein the inspection camera is comprised of an inspection camera and the inspection camera measures a position of the syringe axis relative to the shield axis in step (g).

13. The method of claim 9 wherein the shaker is a pneumatic shaker.

14. The method of claim 9 further comprising:
   (i) moving the shaker out of contact with the nest following step (f).

15. The method of claim 9 wherein the inspection camera measures a distance between a first reference mark on the needle shield and a second reference mark on the syringe in step (g).

16. The method of claim 9 wherein the plug engages the tip end of the syringe following step (d) and the tip is positioned in a cavity defined by the plug.

17. The method of claim 9 further comprising:
   (i) removing the syringe and attached needle shield from the syringe nest following step (h).

18. The method of claim 9 wherein the cap plunger moves from a withdrawn position to a seating position in step (h), the cap plunger being positioned at a predetermined seating distance from the syringe nest in the seating position.

19. The method of claim 18 wherein the cap plunger moves from the withdrawn position to the seating position and, subsequently, back to the withdrawn position in step (h).

20. The method of claim 9 further comprising:
   (j) removing the needle shield from the tip end of the syringe if the inspection of step (g) falls outside of an acceptable tolerance.

* * * * *